(12) United States Patent
Seela et al.

(10) Patent No.: US 6,498,241 B1
(45) Date of Patent: *Dec. 24, 2002

(54) 2-DEOXY-ISOGUANOSINES ISOSTERIC ANALOGUES AND ISOGUANOSINE DERIVATIVES AS WELL AS THEIR SYNTHESIS

(75) Inventors: Frank Seela, Osnabrück (DE); Zigmunt Kasimierczuk, Warszawa (PL); Klaus Mühlegger, Polling (DE); Herbert Von Der Eltz, Weilheim (DE)

(73) Assignee: Roche Diagnostics GmbH, Manneheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/712,454

(22) Filed: Nov. 13, 2000

Related U.S. Application Data (63) Continuation of application No. 09/086,910, filed on May 29, 1998, now Pat. No. 6,147,199, which is a continuation of application No. 08/257,724, filed as application No. PCT/EP92/02843 on Dec. 9, 1992, now abandoned.

(30) Foreign Application Priority Data

Dec. 9, 1991 (DE) .............................................. 4140463

(51) Int. Cl.$^7$ .............................................. C07H 21/04
(52) U.S. Cl. .................... 536/23.1; 536/26.7; 536/27.2; 536/27.6; 536/27.61; 536/27.62; 536/27.63; 536/27.7; 536/27.81; 435/6
(58) Field of Search .......................... 514/44; 536/23.1, 536/26.7, 27.6, 27.61, 27.62, 27.63, 27.7, 27.81, 27.2; 435/6

(56) References Cited

U.S. PATENT DOCUMENTS

| | | | | |
|---|---|---|---|---|
| 5,681,702 A | * | 10/1997 | Collins et al. | .................. 435/6 |
| 5,780,610 A | * | 7/1998 | Collins et al. | ............. 536/24.5 |
| 6,147,199 A | * | 11/2000 | Seela et al. | ................ 536/23.1 |

FOREIGN PATENT DOCUMENTS

| | | | |
|---|---|---|---|
| DE | 4140463 A1 | * | 5/1993 |
| EP | 286028 | | 10/1988 |
| WO | 9003370 | | 5/1990 |
| WO | 9006312 | | 6/1990 |
| WO | WO93/12130 A1 | * | 6/1993 |
| WO | WO96/06970 A1 | * | 3/1996 |

OTHER PUBLICATIONS

Aldrich Chemical Co., *Catalog Handbook of Fine Chemicals*, 1994–1995, Milwaukee, Wisconsin, only p. 74 supplied, see entry 16,496–8 in particular.*

Sigma Chemical Company, *Biochemicals and Reagents for Life Science Research*, 1997, St. Louis, Missouri, only p. 115–116 supplied, see products A8004 to A1768.*

El Khadem (I), *Carbohydrate Chemistry Monosaccharides and Their Oligomers*, Academic Press, New York, NY, 1988, only p. 104–117 supplied.*

El Khadem (II), *Carbohydrate Chemistry Monosaccharides and Their Oligomers*, Academic Press, New York, NY, 1988, only p. 1–8 and 56–63 supplied.*

Switzer, et al., "Enzymatic Incorporation of a New Base Pair Into DNA and RNA", J. Am. Chem. Soc. 111:8322–8323 (1989).

Kazimierczuk, et al., Preparative Photochemical Synthesis of Isoguanosine Ribe–and Deoxyribonucleosides and Nucleotides, and Isouanosine 3'–5'–cyclic phosphate, a new cAMP analogueActa Biochem Polonica 20(4): 395–402 (1973).

Seela, et al., "Furanoside–Pyranoside Isomerization of Tubericiding and its 2'–Deoxy Derivatives—Influence of Nucleobase and Sugar Structure on the Proton Catalyzed Reactoin", J. Chem. Soc. Perkin Trans II 525–530 (1986).

Golas et al., "Preparation and Properties of an Analogue of Poly(G): Poly(isoguanylic acid)", Eur. J. Biochem 65: 183–192 (1976).

Cardinaud, "Thin–layer chromatography of purine bases and deoxyribonucleoside analogues IV", J.Chromatog. 154: 345–348 (1978).

Mantsch, et al., "Structural and Enzymatic Properties of Adenine T–Oxide Nucleotides", Biochemistry 14(26): 5593–5601 (1975).

* cited by examiner

*Primary Examiner*—Johann Richter
*Assistant Examiner*—Lawrence E. Crane
(74) *Attorney, Agent, or Firm*—Pennie & Edmonds LLP (57) ABSTRACT

2'-Deoxyisoguanosine, isosteric analogues and isoguanosine derivatives of formulae I–V, processes for their production via compounds of the general formulae a or b and reaction with aroyl isocyanates or from compounds of the general formulae VI–IX by photochemical irradiation. A further production process is the conversion of deoxyguanosines or guanosines by means of persilylation, reaction with ammonia and deamination in the 2 position. The compounds are suitable as pharmaceutical agents with antiviral efficacy.

15 Claims, 2 Drawing Sheets

FIG. 1

FIG. 2

2-DEOXY-ISOGUANOSINES ISOSTERIC ANALOGUES AND ISOGUANOSINE DERIVATIVES AS WELL AS THEIR SYNTHESIS

This application is a continuation of U.S. application Ser. No. 09/086,910, filed May 29, 1998 now U.S. Pat. No. 6,147,199, which is a continuation of U.S. application Ser. No. 08/257,724, filed Jun. 9, 1994 (now abandoned), which is a 371 of PCT/EP92/02843 filed Dec. 9, 1992 each of which is incorporated herein by reference in its entirety.

Nucleosides are widespread in the living world as building blocks of nucleic acids. They occur as ribonucleosides in ribonucleic acids (RNA) and as deoxyribonucleosides in deoxyribonucleic acids (DNA).

Naturally occurring nucleosides are usually composed of a sugar moiety (ribose or deoxyribose) and an aglyconic heterocyclic moiety. These so-called nucleobases are usually adenine, guanine, cytosine and thymine or uracil.

In addition nucleosides have been found in natural materials that are not components of nucleic acids such as e.g. isoguanosine or 1-methyl-isoguanosine. They often have interesting pharmacological properties.

The object of the present invention was to provide 2'-deoxy-isoguanosines, isosteric derivatives and isoguanosine derivatives as well as their phosphorus compounds. Oligodeoxynucleotides or DNA fragments which contain the compounds according to the invention are suitable for inhibiting the expression of viral genes in biological systems.

Figure 1:
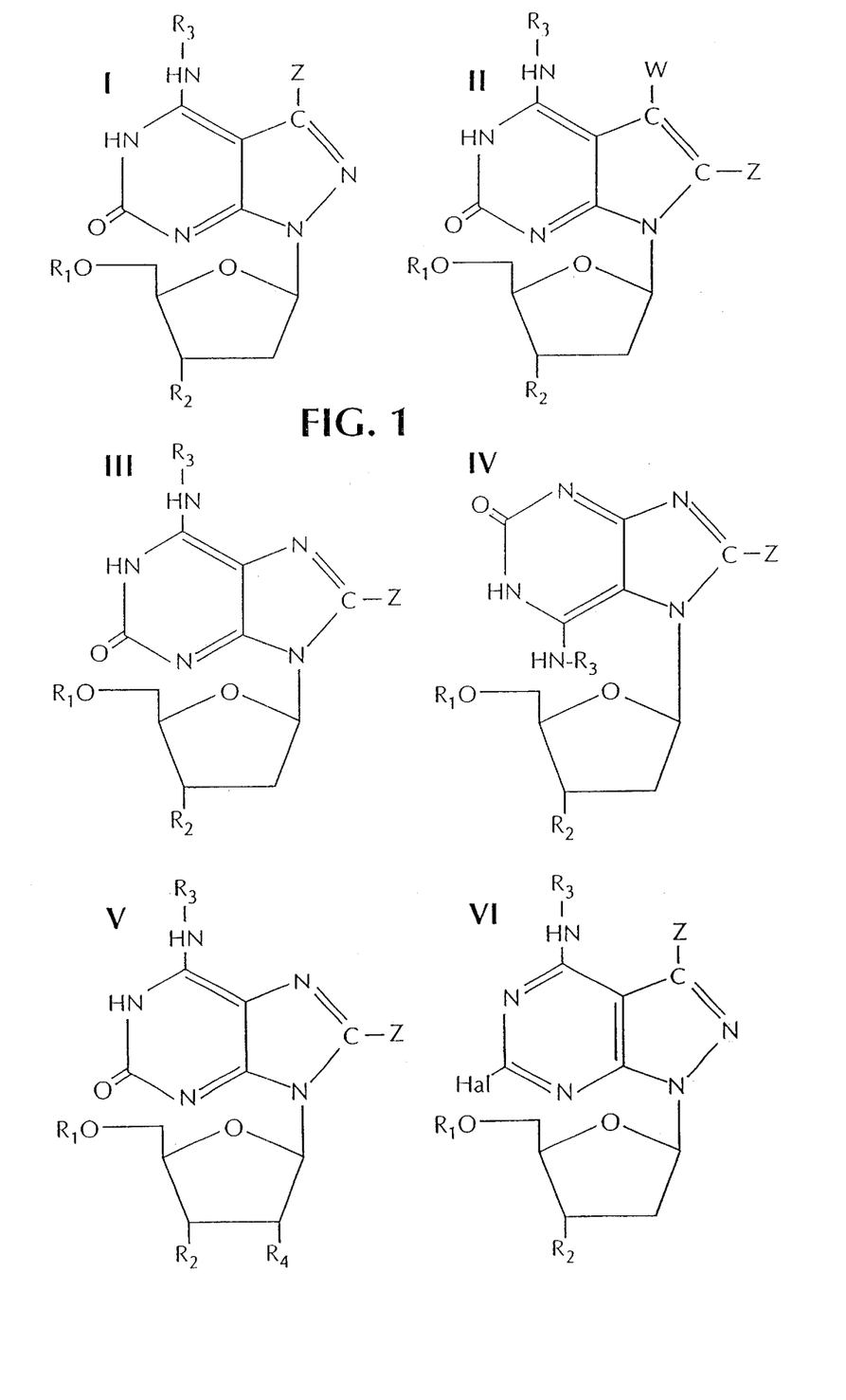
Figure 2:
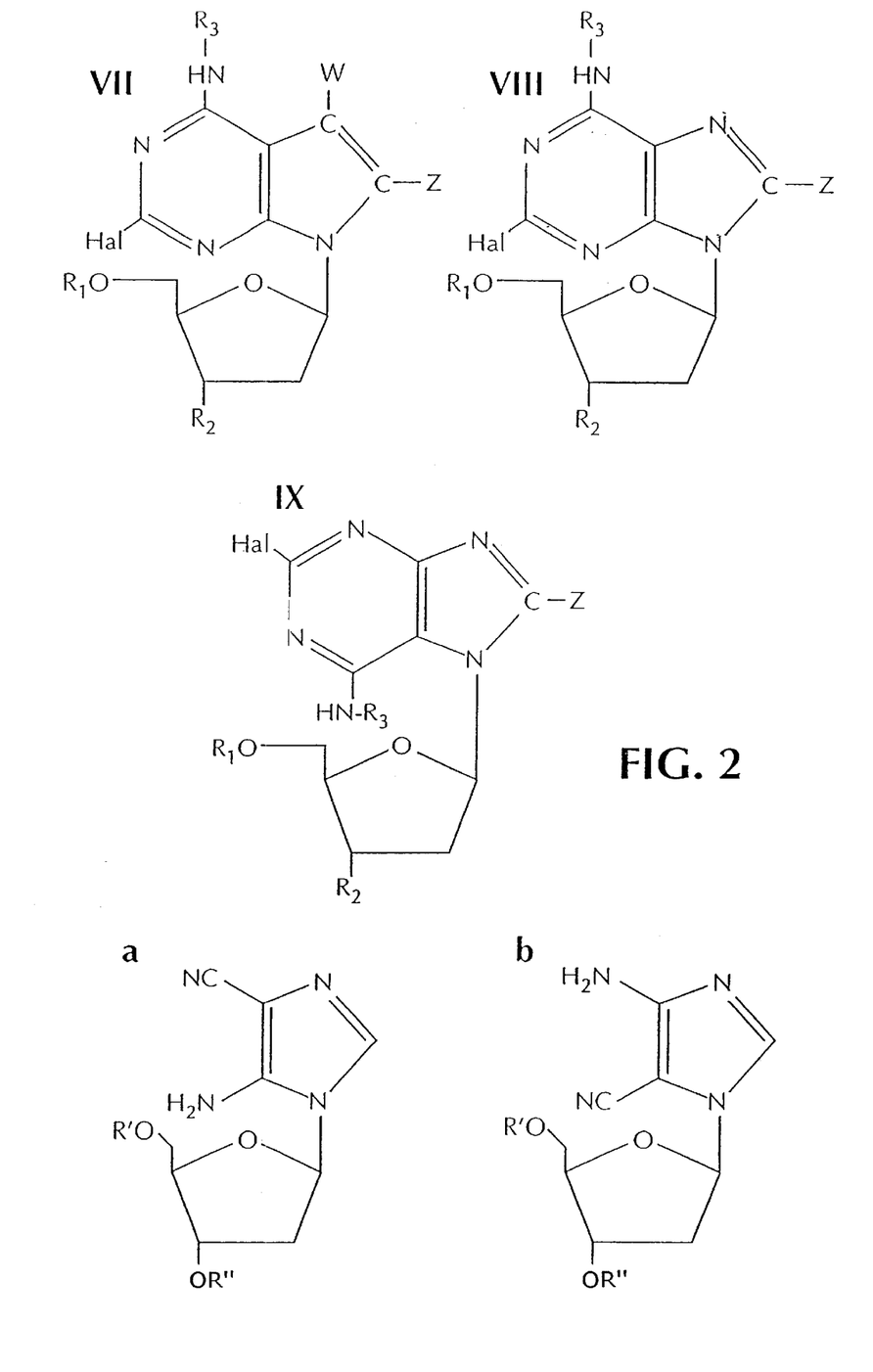

The invention concerns compounds of the general formulae I to IV (cf. FIGS. 1 and 2 for graphic formulae) in which $R_1$=hydrogen or a protecting group, $PO_3H_2$, $P_2O_6H_3$, $P_3O_9H_4$ or the corresponding alpha, beta and gamma thiophosphates provided that $R_1$ does not denote $P_3O_9H_4$ in formula III;

$R_2$=hydrogen, hydroxy, phosphoramidite, methylphosphonate, H-phosphonate, a reporter or intercalator group;

$R_3$=hydrogen or a protecting group;

W or/and Z=hydrogen, halogen, —NH—$(CH_2)_n$NH$_2$(n=2-12), —R—CH$_2$—COOH(R=alkylenyl $C_1$–$C_8$), a reporter or intercalator group.

The invention also concerns compounds of the general formula V in which $R_1$=equals hydrogen or a protecting group, $PO_3H_2$, $P_2O_6H_3$, $P_3O_9H_4$ or the corresponding alpha, beta or gamma thiophosphates;

$R_2$=equals hydrogen, hydroxy, phosphoramidite, H-phosphonate, methylphosphonate, a reporter or intercalator group;

$R_3$=hydrogen or a protecting group;

$R_4$=hydroxy;

Z=hydrogen, halogen, —NH—$(CH_2)_n$NH$_2$(n=2-12), —R—CH$_2$—COOH(R=alkylenyl with $C_1$–$C_8$), a reporter or intercalator group provided that $R_1$, $R_3$ and Z are not simultaneously hydrogen or $R_1$ is not simultaneously $P_2O_6H_3$ when $R_3$ and Z are hydrogen.

The compounds according to the invention of formulae I–IV are produced by either starting with compounds of the general formulae a or b in which R'=R" and represents an acyl protecting group such as e.g. p-toluoyl or benzoyl, this is reacted with aroyl isocyanates e.g. benzoyl isocyanate and the desired isoguanosine is isolated, or compounds of the general formulae VI to IX in which W, Z, $R_1$, $R_2$ and $R_3$ have the above-mentioned meanings, and Hal represents chlorine, bromine or iodine are converted photochemically by irradiation into the 2'-deoxyisoguanosines.

Compounds of the general formula V are produced analogously in which case one starts with compounds of formulae a, b, VI to IX which contain a β-D-ribo-furanosyl residue instead of the β-D-erythro-pentofuranosyl residue.

A particularly preferred process for the production of the compounds according to the invention is to persilylate deoxyguanosine or guanosine and their derivatives with hexamethyldisilazane and trimethyl-chlorosilazane. Subsequently the 2,6-diaminonucleoside is produced using ammonia and tris(trimethyl)silyl-triflate and selectively deaminated in the 2 position using nitrite to the isoguanosine or deoxyguanosine.

The further derivatization is carried out according to methods well known to a person skilled in the art.

The heterocyclic moiety in the 2'-deoxyisoguanosines and isoguanosines according to the invention can be preferably replaced by the corresponding isosters 7-deaza-isoguanine and 7-deaza-8-aza-isoguanine in which case these bases can in addition contain further substituents on the C-7 of the 7-deaza- or 7-deaza-8-aza-isoguanine and on the C-8 of isoguanine. Such substituents can for example be reporter groups as described below.

Hydrogen, halogen, NH—$(CH_2)_n$NH$_2$, R—CH$_2$COOH, a reporter or intercalator group are particularly preferred.

A diamino group can be introduced at position W and/or Z by halogenating a compound in which W and/or Z is hydrogen (for example with bromine water) and introducing a diamino group in the bromide by nucleophilic substitution. A diaminopentyl or diaminohexyl group is particularly preferably introduced. The desired compound can be prepared from the mixture of amino compounds by chromatographic purification.

A carboxyl group can be introduced by reacting the corresponding halogenated compound with methyllithium and preparing methyl bromide with halogen. This compound is reacted with aminocarboxylic acids (e.g. amino-caproic acid) to form the final product.

The reporter or intercalator groups are preferably coupled in their activated form (e.g. hydroxysuccinimide ester) to the amino or carboxyl group of the compounds according to the invention.

All suitable end groups known to a person skilled in the art can be present on the 3' and 5' end of the sugar moiety of the compounds according to the invention. Hydrogen, monophosphate, diphosphate or triphosphate, a reporter group or intercalator group are preferred for the 3' end and for the 5' end. A reporter group within the meaning of the invention is understood as a hapten such as biotin or digoxigenin or a fluorescent dye. Suitable intercalator groups are described by Hélène, C. in "Antisense RNA and DNA, Curr. Commun. Mol. Biol.; Cold Spring Harbor Laboratory, Cold Spring Harbor, N.Y., 1987" and are preferably phenanthroline, acridine, actinomycin or its chromophore or heavy metal complexing agents such as EDTA. Groups which result in a cross-linking of nucleic acids such as e.g. psoralen are also advantageous.

Cyclic phosphoric acid diesters (3', 5'-cyclophosphates) can be produced from the compounds according to the invention by water liberation between the 3'-OH and 5'-OH of the sugar moiety.

The production of phosphoramidites, H-phosphonates and p-methylphosphoramidites from isoguanosines is carried out analogously to the production of the corresponding deoxyisoguanosine derivatives in which case the 2'-OH group is preferably protected by a triisopropylsilyl group.

The invention in addition concerns 2'-deoxyisoguanosines, isoguanosines and 7-deaza-8-aza-isoguanosine-3'-phosphoramidites, -3'-H-phosphonates and —P-methyl-phosphoramidites protected by bases and sugars. These compounds are suitable as nucleotide building blocks for the production of oligonucleotides.

The nucleotide building blocks according to the invention preferably contain protecting groups on the heterocyclic bases as well as on the 5'-OH and/or 2'-OH groups of ribose.

Amino-protecting groups such as e.g. benzoyl, formamidine, isobutyryl or diphenoxyacetyl groups are preferably used as a protecting group on the heterocyclic bases.

The 5' or 2'-OH protecting group of the sugar moiety is preferably a triphenylmethyl, monomethoxytrityl, dimethoxytrityl, t-butyl-dimethylsilyl, t-butyldiphenylsilyl, t-butyl-methoxyphenylsilyl or pixyl group 3'-O-(2-cyanoethyl)-N,N-diisopropyl-aminophosphanes and 3'-O-methyl-N,N-diisopropylamino-phosphanes are preferred as phosphoramidites. The H-phosphonates are preferably used as salts.

The production of the monomeric nucleotide building blocks is carried out according to methods familiar to a person skilled in the art such as those described by Gait, M. J. in "Oligonucleotide Synthesis, A Practical Approach", IRL Press, Ltd. (1984).

The compounds according to the invention of the general formulae I to IX can be incorporated by DNA or RNA polymerases into oligonucleotides or newly synthesized DNA or RNA in the form of their respective 5'-triphosphates or α-, β- or γ-thiotriphosphates.

In a particularly preferred embodiment, these nucleotide building blocks according to the invention are labelled with $^{32}P$ or $^{35}S$.

The invention therefore also concerns a process for the production of oligonucleotides and polynucleotides which contain the compounds according to the invention as building blocks. Such processes can be of a chemical as well as of an enzymatic nature.

The chemical synthesis of oligonucleotides is carried out according to methods known to a person skilled in the art as described for example in Gait, M. J., loc. cit. or in Narang, S. A., "Synthesis and Application of DNA and RNA", Academic Press, 1987.

The production of the oligonucleotides according to the invention is carried out in a known manner, for example according to the phosphate triester, the phosphite triester or H-phosphonate method in a homogeneous phase or on a support. The two latter methods are preferably used whereby the synthesis is usually carried out using automated synthesizers. The support materials in this case consists of inorganic (controlled pore glass, Fractosil) or organic polymeric material (e.g. polystyrene) known to a person skilled in the art.

The invention therefore also concerns a process for the production of oligonucleotides consisting of 6 to 100 nucleotide building blocks according to the oligonucleotide synthesis process in which, depending on the sequence design, appropriate 2'-deoxy-isoguanosines or isoguanosines according to the invention are used wherein a starting nucleoside is bound to a solid support and subsequently the desired oligonucleotide is assembled by stepwise coupling using appropriately activated monomeric nucleotide building blocks, if desired trivalent phosphorus is oxidized to pentavalent phosphorus during or after the synthesis, the oligonucleotide is cleaved from the support with a first base, heterocyclic protecting groups are cleaved with a second base, the 5' protecting group is cleaved with an acid and the oligonucleotide is purified if desired. The purification is preferably carried out by reverse phase or anion exchange HPLC. This is usually followed by a desalting, for example by dialysis.

In addition the oligonucleotides according to the invention can also be produced enzymatically using polymerases. Such processes are known to a person skilled in the art under the terms "in vitro transcription", "nick translation" [Rigby et al., J. Mol. Biol. 113, 237 (1977)] and "random priming" [Feinberg, A. P. and Vogelstein, B., Anal. Biochem. 137, 266 (1984)].

In this process 2'-deoxynucleoside-5'-triphosphates or isoguanosine-5'-triphosphates are basically incorporated by polymerases using a single-stranded template nucleic acid and a starter molecule (primer/promoter) into a newly synthesized second strand that is complementary to the bases of the first strand. The use of the nucleoside-5'-triphosphates according to the invention and their corresponding substituted derivatives enables suitable signal groups or reporter groups such as haptens or fluorophores to be incorporated for example into nucleic acids. Such techniques are widely used nowadays for example in the form of non-radioactive labelling of biomolecules.

The invention in addition concerns the use of oligonucleotides in which guanosine or deoxyguanosine building blocks have been replaced completely or partially by the deoxyisoguanosine or isoguanosine building blocks according to the invention and which are composed of 6 to 100 nucleotide building blocks for the production of a pharmaceutical agent with antiviral activity.

Oligonucleotides containing 2'-deoxyisoguanosine form duplex and triplex structures and also aggregates with themselves as well as with other conventional and modified oligonucleotides. In the case of 2'-deoxyisoguanosine this results in manifold base pairing patterns which differ from those of 2'-deoxyguanosine and in which the oligonucleotide strands can be arranged either in parallel or antiparallel.

a) Aggregate Structures

During the preparation of 2'-deoxyisoguanosine it is noticed that it forms gels like 2'-deoxyguanosine and crystallizes with extreme difficulty. Aggregates have been demonstrated by gel electrophoresis for oligonucleotides containing guanine [66] which comply with the structural proposal of Zimmerman [67].

In this structure all $N^7$ atoms are bound up in a Hoogsteen base pairing. The $(iG_d)_4$ structure differs considerably from the $(G_d)_4$ configuration since in this case two $N^7$ atoms and two $N^3$ atoms act in addition to the 0 atoms as proton acceptors. As a result 2'-deoxyisoguanosine is able to form a dimeric structure in which one molecule is present as a 1H tautomer and the other as a 3H tautomer.

An interaction via N-7 is not possible in the case of 7-deazapurine derivatives such as 7-deaza-2'-deoxyisoguanosine and 7-deaza-8-aza-2'-deoxyisoguanosine. Hence no aggregate formation is observed with these compounds.

b) Watson-Crick Duplex Structures

With regard to the complexation of single-stranded DNA or RNA, oligonucleotides containing $iG_d$ are able to form duplex structures. In this process parallel and antiparallel configurations of the strands are possible. Due to the altered pattern of substituents on the base and the possible parallel duplex structures, an increased stability towards nucleases would be expected.

c) Triplex Structures of DNA Duplexes with Oligonucleotides Containing $iG_d$

Oligonucleotides which contain 2'-deoxyisoguanosine as monomeric building blocks can form triplex structures with d(AT) duplexes as well as with d(GC) duplexes. In both cases these structures can form in a neutral medium; a protonation is not necessary. As a result the complexation can be achieved under physiological conditions.

The structures discussed above apply in principle to oligoribonucleotides and oligodeoxyribonucleotides.

[66] J. Kim, Ch. Cheong and P. B. Moore, 'Tetramerization of an RNA oligonucleotide containing a GGGG sequence', Nature 1991, 351, 331.

[67] S. B. Zimmerman, 'X-ray Study by Fiber Diffraction Methods of a Self-aggregate of guanosine-5'-phosphates with the same Helical Parameters as Poly (rG)', J. Mol. Biol. 1976, 106, 663.

The oligonucleotides according to the invention and their salts can be used as medicines e.g. in the form of pharmaceutical preparations which can be administered orally e.g. in the form of tablets, coated tablets, hard or soft gelatin capsules, solutions, emulsions or suspensions. They can also be administered rectally e.g. in the form of suppositories or parenterally e.g. in the form of injection solutions. These compounds can be processed in therapeutically inert organic and inorganic carriers for the production of pharmaceutical preparations. Examples of such carriers for tablets, coated tablets and hard gelatin capsules are lactose, maize starch or derivatives thereof, talcum, stearic acid or salts thereof. Suitable carriers for the production of solutions are water, polyols, sucrose, inverted sugar and glucose. Suitable carriers for injection solutions are water, alcohols, polyols, glycerol and vegetable oils. Suitable carriers for suppositories are vegetable and hardened oils, waxes, fats and semi-liquid polyols.

The pharmaceutical preparations can also contain preservatives, solvents, stabilizers, wetting agents, emulsifiers, sweeteners, dyes, flavourings, salts to change the osmotic pressure, buffers, coating agents or antioxidants as well as if desired other therapeutically-active substances.

The invention is elucidated in more detail by the following examples:

EXAMPLE 1

2'-Deoxy-isoguanosine[9-(2-deoxy-β-D-erythro-pentofuranosyl)-9H-isoguanine

Method A: 0.6 ml (4.3 mmol) benzoyl isocyanate is added at room temperature while stirring to a solution of 400 mg (0.87 mmol) 5-amino-1-[2'-deoxy-3',5'-di-O-(p-toluoyl)-β-D-erythro-pentofuranosyl)-4-imidazocarbonitrile in 15 ml dry acetonitrile. A precipitate forms within 15 minutes. The reaction mixture is stirred overnight and afterwards refluxed for 30 minutes. The solvent is removed by distillation, the residue is dissolved in 100 ml of a mixture of isopropanol/25% aqueous ammonia solution (1:1) and the solution is stirred for 2 days at room temperature. After evaporation, the residue is extracted twice with 50 ml ether each time while stirring. The residue is taken up in 100 ml water to which a few drops of 25% ammonia solution have been added and filtered. The filtrate is concentrated to a volume of about 30 ml and applied to a XAD-4 column (20×2 cm). The inorganic salts are removed by elution with 200 ml water, elution with water/ isopropanol (9:1) affords the desired product. After evaporation, the residue is crystallized from ethanol.

Yield: 100 mg=43% of theoretical yield.

Colourless crystals which melt above 230° C. with decomposition.

TLC (cellulose, mobile solvent water-saturated n-butanol): Rf=0.25

UV (pH 1): $\lambda_{max}$ 235 nm (5200), 284 (11500); (pH 7): 247 (9100), 292 (10100) (pH 13): 249 (6600), 284 (9800).

$^1$H-NMR ($d_6$DMSO): 2.18, 2.30 (2m, 2H, C-2'); 3.55 (m, 2H, C-5'); 3.84 (m, 1H, C-4'); 4.35 (m, 1H, C-3'); 5.30 (bs, 2H, OH—C-3' and OH—C-5'); 6.11 (t, J=6.4 Hz, 1H, C-1'); 7.95 (s, 1H, C-8); 8.1 (bs, $NH_2$).

Elemental analysis $C_{10}H_{13}N_5O_4$: calc. C, 44.94; H, 4.90; N, 26.21; found C, 44.70; H, 5.03; N, 25.99.

Method B: A solution of 200 mg (0.61 mmol) 2-bromo-2'-deoxyadenosine in 250 ml water is irradiated for 30 minutes in a quartz reactor (equipped with a 30 W sterilisation lamp Philips/Holland; the radiation is passed through a 2 mm layer of 20% acetic acid in order to filter out light below 230 nm). The pH is then adjusted to 8.0 with ammonia solution, it is concentrated to a volume of ca. 20 ml and applied to an XAD-4 column (21×3 cm). The elution is carried out with a gradient of water to 50% methanol whereby the desired product is eluted at 15–20% methanol. The pooled main fraction is evaporated and the residue is crystallized from ethanol.

Yield: 85 mg=53% of theoretical yield.

The material is chromatographically identical to that obtained in method A and with regard to its spectral data.

2'-Deoxy-isoguanosine is obtained in 52% yield in an analogous manner from 2-chloro-2'-deoxy-adenosine after an irradiation period of 1 hour.

EXAMPLE 2

7-(2-Deoxy-β-D-erythro-pentofuranosyl)-7H-isoguanine 0.27 ml (1.95 mmol) benzoyl isocyanate is added at room temperature while stirring to a solution of 300 mg (0.65 mmol) 4-amino-1-(2'-deoxy-3',5'-di-O-(4-toluoyl)-β-D-erythro-pentofuranosyl)-1H-imidazole-5-carbonitrile in 15 ml absolute acetonitrile. A white precipitate forms after 1 hour; the suspension is stirred overnight, evaporated to dryness and isopropanol/25% aqueous ammonia solution (75 ml, 1:1) is added. After stirring for 2 days at room temperature, the solvent is removed by evaporation, the residue is taken up in 75 ml diethylether/ethyl acetate (1:1) and stirred for 1 hour at room temperature. The supernatant solution is decanted off and the residue is admixed with 75 ml water as well as 2 drops of 25% aqueous ammonia solution. After stirring for a short time, it is filtered, the filtrate is concentrated to 40 ml and applied to an Amberlite XAD-4 column (25×3 cm). After washing with 200 ml water, the main product is eluted with 10% aqueous isopropanol and subsequently the solvent is removed by evaporation. It is crystallized from ethanol.

Yield: 110 mg=63% of theoretical yield.

Colourless crystals which melt above 230° C. with decomposition.

TLC (cellulose, mobile solvent water-saturated n-butanol): Rf=0.15

UV (pH 1): $\lambda_{max}$ 290 (8600); (pH 7): 282 (7100), 242 (7000); (pH 13): 285 (5700).

$^1$H-NMR ($d_6$DMSO): 2.25, 2.40 (2m, 2H, C-2'); 3.55 (m, 1H, C-5'); 3.84 (m, 1H, C-4'); 5.35 (bs, 3'-OH, 5'-OH); 6.12 (pt, J=6.6 Hz, 1H, C-1'); 7.27 (bs, 2H, $NH_2$); 8.19 (s, 1H, C-8).

Elemental analysis $C_{10}H_{13}N_5O_4$: calc. C, 44.94; H, 4.90; N, 26.2; found C, 44.78; H, 5.05; N, 25.82.

EXAMPLE 3

7-Deaza-2'-deoxy-isoguanosine-5'-triphosphate[4-amino-7-(2-deoxy-5-triphosphate-β-D-erythro-pentofuranosyl)-3H,7H-pyrrolo[2,3-d]-pyrimidin-2-one]

Step 1: 7-deaza-2'-deoxy-isoguanosine

A solution of 85 mg (0.3 mmol)4-amino-2-chloro-7-(2'-deoxy-β-D-erythro-pentofuranosyl)-7H-pyrrolo[2,3-d]-pyrimidine is dissolved in 200 ml water containing 1 ml concentrated aqueous ammonia solution and the solution is irradiated for 1 hour in a quartz reactor as described in example 1, method B. The solution is subsequently concentrated to 30 ml and applied to a XAD-4 column (20×2 cm). The resin is subsequently washed with 150 ml water, afterwards it is eluted with ca. 1 l of a mixture of water/isopropanol 9:1. The fractions containing the nucleoside are pooled and evaporated. The residue is crystallized from ethanol.

Yield: 46 mg=58% of theoretical yield.

Colourless needles of melting point 230° C.

Elemental analysis $C_{11}H_{14}N_4O_4$: calc. C, 49.62; H, 5.30; N, 21.04; found C, 49.7; H, 5.4; N, 21.1.

Step 2: 7-deaza-2'-deoxy-isoguanosine-5'-triphosphate

The nucleoside from step 1 was converted into the 5'-monophosphate according to Yoshikawa et al. [Tetrah. Lett. 50, 5065 (1967)]; the desired triphosphate was obtained therefrom according to the method of Hoard and Ott [J. Am. Chem. Soc. 87, 1785 (1965)].

$^{31}$P-NMR (0.1 M EDTA/D$_2$O/Eth$_3$N): −8.20 (d, P-g), −10.5 (d, P-a), −21.2 (t, P-β)

EXAMPLE 4

4-Amino-6-chloro-1-(2-deoxy-β-D-erythro-pentofuranosyl)-1H-pyrazolo[3,4-d]-pyrimidine A suspension of 540 mg (1 mmol) 1-{2'-deoxy-3',5'-di-O-(4-toluoyl)-β-D-erythro-pentofuranosyl}-4,6-dichloro-1H-pyrazolo[3,4-d]-pyrimidine in 40 ml methanolic ammonia solution (saturated at 0° C.) is stirred for 2 days at 60° C. The reaction mixture is then evaporated to dryness and the residue is chromatographed on a silica gel 60 H column (15×4 cm) using CH$_2$Cl$_2$/methanol (9:1).

Yield: 200 mg=70% of theoretical yield

Recrystallization from water yields colourless needles of melting point 183–185° C.

TLC (silica gel, mobile solvent CH$_2$Cl$_2$/methanol 9:1): Rf=0.45.

UV (pH 1): $\lambda_{max}$=265 (10150); (pH 7): 271.5 (10350).

$^1$H-NMR (d$_6$DMSO): 2.45, 2.75 (2m, 2H, C-2'); 3.50 (m, 2H, C-5'); 3.81 (q, 1H, C-4'); 4.41 (bs, 1H, C-3'); 4.71 (t, OH—C-5'); 5.27 (d, OH—C-3'); 6.44 (t, J=6.2 Hz, 1H, C-1'); 8.16 (bs, NH$_2$); 8.34 (s, 1H, C-3).

Elemental analysis $C_{10}H_{12}N_5O_3Cl$: calc. C, 42.04; H, 4.23; N, 24.51; found C, 42.29; H, 4.27; N, 24.48.

EXAMPLE 5

4-Amino-1-(2-deoxy-β-D-erythro-pentofuranosyl)-1H-pyrazolo[3,4-d]-pyrimidin-6-(5H)-one A solution of 105 mg (0.37 mmol) 4-amino-6-chloro-1-(2'-deoxy-β-D-erythro-pentofuranosyl)-1H-pyrazolo[3,4-d]pyrimidine is dissolved in 200 ml water containing 1 ml concentrated ammonia solution and irradiated for 1 hour in a quartz reactor. The processing is carried out as described in example 3.

Yield: 57 mg=58% of theoretical yield.

Colourless powder, melting point 235° C. (decomp.)

TLC (cellulose, water-saturated n-butanol): R$_f$ 0.3

UV (pH 1): 268 (8500); (pH 7): 221 (21200), 251 (7900), 283 (6700); (pH 13): 221 (26600), 255 (6600), 278 (9000).

$^1$H-NMR (d$_6$DMSO): 2.20, 2.52 (2m, 2H—C-2'); 3.3 (m, 2H, C-5'); 3.64 (q, H, C-4'); 4.21 (bs, H, C-3'); 5.1 (bs, OH—C-3' and OH—C-5'); 6.12 (t, J=6.4, H—C-1'); 7.79 (s, H—C-3); 8.1 (NH$_2$).

Elemental analysis $C_{10}H_{13}N_5O_4$: calc. C, 44.94; H, 4.90; N, 26.2; found C, 44.89; H, 5.0; N, 25.89.

EXAMPLE 6

9-(2-Deoxy-β-D-erythro-pentofuranosyl)-6-[1-(dimethylamino)methylene]-9H-isoguanine (5)

200 mg (0.74 mmol) 2'-deoxy-isoguanosine from example 1 is dissolved in 10 ml absolute dimethylformamide and admixed with 1.3 ml (7.6 mmol) N,N-dimethylformamide-diethylacetal. It is stirred for 24 hours at room temperature, concentrated in a vacuum and the residue is evaporated several times with toluene and acetone. Subsequently it is chromatographed on silica gel 60 H (25×4.5 cm column, eluting agent chloroform/methanol 8:2). The main fractions are pooled, the solvent is removed by evaporation and the residue is recrystallized from methanol.

Yield: 150 mg=62% of theoretical yield

Pale yellow crystals of melting point 178° C. (decomp.).

TLC (silica gel, chloroform/methanol 8:2) R$_f$=0.62

UV (methanol: $\lambda_{max}$=338 (9400), 259 (6100), 223 (9100).

$^1$H-NMR (d$_6$DMSO): 2.20, 2.64 (2m, 2H, C-2'); 3.12, 3.22 (2s, 4H, (CH$_3$)$_2$N); 3.50 (2m, 2H, C-5'); 3.86 (m, 1H, C-4'); 4.38 (m, 1H, C-3'); 5.10 (t, 1H, OH—C-5'); 5.31 (d, 1H, OH—C-3'); 6.15 (pt, J=6.25 Hz, 1H, C-1'); 8.08 (s, 1H, C-8); 9.2 (s, 1H, —N═CH).

Elemental analysis: $C_{13}H_{18}N_6O_4$: calc. C, 48.44; H, 5.63; N, 26.07; found C, 48.25; H, 5.69; N, 25.87.

EXAMPLE 7

7-(2-Deoxy-β-D-erythro-pentofuranosyl)-6-[1-(dimethylamino)methylidene]-7H-isoguanine 300 mg (1.12 mmol) 7-(2'-deoxy-β-D-erythro-pentofuranosyl)-7H-isoguanine is dissolved in 10 ml absolute dimethylformamide and admixed with 2 ml (11.7 mmol) N,N-dimethylformamide-diethylacetal and stirred for 24 hours at room temperature. The processing is carried out as described in example 6.

Yield: 62 mg=72% of theoretical yield.

Pale yellow crystals of melting point 208–209° C.:

TLC (silica gel, chloroform/methanol 8:2): R$_f$=0.56

UV (methanol) $\lambda_{max}$=326 (7800), 296 (6700), 245 (3200).

$^1$HMR (d$_6$DMSO): 2.30 2.43 (2m, 2H, C-2'); 3.14, 3.23 (2s, 4H, (CH$_3$)$_2$N); 3.49 (2m, 2H, C-5'); 3.9 (m, 1H, C-4'); 4.30 (m, 1H, C-3'); 5.10 (t, 1H, OH—C-5'); 5.31 (d, 1H, OH—C-3'); 6.84 (pt, J=6.25 Hz, 1H, C-1'); 8.32 (s, 1H, C-8); 8.8 (s, 1H, —N═CH).

Elemental analysis: $C_{13}H_{18}N_6O_4$: calc. C, 48.44; H, 5.63; N, 26.07; found C, 48.29; H, 5.73; N, 25.91

EXAMPLE 8

9-(2-Deoxy-β-D-erythro-pentofuranosyl)-6-[1-(dimethylamino)methylidene]-2-chloro-adenine 300 mg (1.05 mmol) 2-chloro-2'-deoxy-adenosine [produced according to Z. Kazimierczuk et al., J. Am. Chem. Soc. 106, 6379 (1984)] is dissolved in 3 ml anhydrous DMF and 0.9 ml (5.2 mmol) N,N-dimethylformamide-diethylacetal is added. It is stirred for 1 hour at room temperature, concentrated and the residue is evaporated several times with toluene. Subsequently it is chromatographed on silica gel 60 H (15×5 cm column, eluting agent dichloromethane/methanol 9:1).

Yield: 295 mg=82.4% of theoretical yield.

Colourless, foamy product.

The 7-regioisomers can be synthesized in an analogous manner according to Z. Kazimierczuk.

EXAMPLE 9

9-[2-Deoxy-5-O-(4,4'-dimethoxytriphenyl-methyl)-β-D-erythro-pentofuranosyl]-6-[1-(dimethylamino)methylidene]-2-chloro-adenine 340 mg (1 mmol) of the compound from example 8 is dried by evaporating several times with anhydrous pyridine and subsequently dissolved in 2 ml pyridine. After addition of 440 mg (1.3 mmol) 4,4'-dimethoxytriphenylmethyl chloride, it is stirred for 1 hour at room temperature. Afterwards it is hydrolysed with 30 ml of a 5% aqueous $NaHCO_3$ solution and extracted three times with 50 ml dichloromethane each time. The combined organic phases are dried over $Na_2SO_4$, filtered and the solvent is removed. After chromatography on silica gel 60 H (20×5 cm column, mobile solvent dichloromethane/ methanol 9:1) and evaporating the main fraction, the product is obtained as an amorphous material.

Yield: 390 mg=60% of theoretical yield.

TLC (silica gel, mobile solvent dichloromethane/ methanol 9:1): $R_f$=0.41

UV (methanol): $\lambda_{max}$=314 (27200), 236 (30500).

$^1$H-NMR ($d_6$DMSO): 2.37, 2.82 (2m, 2H, C-2'); 3.14, 3.22 (2S,, 6H, $(CH_3)_2$N); 3.69, 3.71 (2s, 6H, 2×O—$CH^3$); 3.98 (m, 1H, C-4'); 4.46 (m, 1H, C-3'); 5.39 (d, J=4.5 Hz, 1H, OH—C-3'); 6.35 (pt, J=6.2 Hz, 1H, C-1'); 6.72–7.3 (m, 13H, arom.); 8.37 (s, 1H, C-8); 8.84 (s, 1H, —N=CH).

Elemental analysis $C_{34}H_{35}N_6O_5Cl$: calc. C, 63.49; H, 5.49; N, 13.06; found C, 63.30; H, 5.68; N, 12.88.

EXAMPLE 10

9-[2-Deoxy-3-(H-phosphonato)-5-O-(4,4'-dimethoxytriphenyl-methyl)-β-D-erythro-pentofuranosyl]-6-[1-(dimethylamino)methylidene]-2-chloro-adenine 358 mg (5 mmol) 1,2,4-triazole is added under an argon atmosphere at room temperature to a solution of 12 ml absolute $CH_2Cl_2$, 135 μl (1.55 mmol) $PCl_3$ and 1.7 ml (15.2 mmol) N-methylmorpholine. After stirring for 30 minutes, the reaction solution is cooled to 0° C. and admixed within 10 minutes with a solution of 200 mg (0.31 mmol) of the compound from example 9 in 10 ml $CH_2Cl_2$. It is stirred for a further 20 minutes at room temperature and subsequently 17 ml 1 M triethylammonium bicarbonate buffer (TBK) (pH 7.7) is added. The aqueous phase is extracted three times with 15 ml $CH_2Cl_2$ in each case, the combined organic phases are dried over $Na_2SO_4$ and the dichloromethane is removed by evaporation. After chromatography on silica gel 60 H (20×5 cm column, elution firstly with 1 1 dichloromethane/triethylamine 98:2, then with dichloromethane/methanol/triethylamine 88:10:2), the main fractions are pooled, the solvent is removed, the residue is taken up in 20 ml $CH_2Cl_2$ and shaken out several times with 0.1 M TBK buffer. The combined organic phases are dried over $Na_2SO_4$ and concentrated.

Yield: 190 mg=73% of theoretical yield.

TLC (silica gel, mobile solvent dichloromethane/ methanol/triethylamine 88:10:2): $R_f$=0.37

UV (methanol): $\lambda_{max}$=316 (19900), 235 (21200).

$^1$H-NMR ($d_6$DMSO): 0.9–1.2 (m, 9H, HN$(CH_2CH_3)_3$); 2.92 (2m, 2H, C-2'); 2.60–2.64 (m, 6H, NH$(CH_2CH_3)_3$); 3.14, 3.23 (2s, 6H, $(CH_3)_2$N9; 3.69, 3.71 (2s, 6H, 2×$OCH_3$); 4.16 (m, 1H, C-4'); 4.77 (m, 1H, C-3'); 6.63 (d, 1H, H-phosphonate); 6.34 (pt, 1H, C-1'); 6.73–7.3 (m, 13H, arom.); 8.34 (s, 1H, C-8); 8.85 (s, 1H, —N=CH).

$^{31}$P-NMR ($d_6$DMSO): 1.09 ppm ($^1$J (P—H)=585.3 Hz, $^3$J (P—H)=9.1 Hz). Elemental analysis $C_{40}H_{51}N_7O_7ClP$: .calc. C, 59.43; H, 6.36; N, 12.13; found C, 59.26; H, 6.50; N, 11.93.

EXAMPLE 11

9-[2-Deoxy-5-O-(4,4'-dimethoxytriphenyl-methyl)-β-D-erythro-pentofuranosyl]-6-[1-(dimethylamino)methylidene]-9H-isoguanine 322 mg (1 mmol) of the compound from example 6 is converted into the desired 5'-dimethoxytrityl-protected nucleoside as described in example 9.

Yield: 355 mg=57% of theoretical yield.

TLC (silica gel, dichloromethane/methanol 9:1): $R_f$=0.32

$^1$H-NMR ($d_6$DMSO): 2.35, 2.7 (2m, 2H, C-2'); 3.14, 3.24 (2s, 6H, $(CH_3)_2$N); 3.61, 3.69 (2s, 6H, 2×$OCH_3$); 4.10 (m, 1H, C-4'); 4.41 (m, 1H, C-3'); 5.28 (d, J=4.5 Hz, 1H, OH—C-3'); 6.40 (pt, J=6.2 Hz, 1H, C-1'); 6.68–7.2 (m, 13H, arom.); 8.4 (s, 1H, C-8); 8.8 (s, 1H, —N=CH).

Elemental analysis $C_{34}H_{36}N_6O_6$: calc. C, 65.37; H, 5.81; N, 13.45; found C, 65.23; H, 5.92; N, 13.18.

EXAMPLE 12

Carrier (Fractosil)-bound 9-[2-deoxy-5-O-(4,4'-dimethoxytriphenyl-methyl)-β-D-erythro-pentofuranosyl]-6-[1-(dimethylamino)methylidene]-9H-isoguanine 75 mg (0.6 mmol) N,N-dimethylamino-pyridine and 250 mg (2.5 mmol) succinic acid anhydride are added to a solution of 312.3 mg (0.5 mmol) of the completely protected nucleoside from example 11 in 15 ml dry pyridine and the reaction mixture is stirred for 72 hours at 40° C. After addition of 5 ml water, it is evaporated to dryness and the residue is rotary evaporated with 50 ml toluene. It is dissolved in 100 ml dichloromethane and extracted in succession firstly with 30 ml 10% aqueous citric acid solution and then with 30 ml water. After drying the organic phase over $Na_2SO_4$, the solvent is removed by distillation. 335 mg (nearly the theoretical yield) of the succinate is obtained which is reacted without further purification. For this it is dissolved in 2.5 ml of a 5% solution of pyridine in dioxane and admixed with 120 mg (0.9 mmol) p-nitrophenol and 206 mg (1 mmol) dicyclohexylcarbodiimide. It is stirred for 3 hours at room temperature, the precipitated dicyclohexylurea is removed by suction filtration and 3 ml DMF, 600 mg Fractosil® 200 (Merck, 450 µeq $NH_2$/g) and 0.625 ml triethylamine are added to the filtrate. It is shaken for 4 hours at room temperature, then 0.2 ml acetic anhydride is added and it is shaken for a further 30 minutes. The silica gel containing the bound nucleoside is suction filtered, washed in succession with DMF, ethanol and ether, and dried in a vacuum.

The loading of the carrier with nucleoside was determined as follows:

5 mg Fractosil carrier was treated with 10 ml 0.1 m p-toluenesulfonic acid in acetonitrile. After standing for 10 minutes, the supernatant was measured spectrophotometrically at 498 nm in which case a loading of 35 µmol nucleoside per gram carrier was found ($A_{DMT}$=70,000).

EXAMPLE 13

9-[2-Deoxy-3-(2-cyanoethyl)-N,N-diisopropyl-phosphoramidite-5-O-(4,4'-dimethoxytriphenyl-methyl)-β-D-erythro-pentofuranosyl]-6-[1-(dimethylamino)methylene]-9H-isoguanine 312.3 mg (0.5 mmol) of the protected nucleoside from example 11 is dissolved in 5 ml dry tetrahydrofuran and 0.275 ml (1.6 mmol) ethyldiisopropylamine is added. Subsequently 0.125 ml (0.55 mmol) chloro-β-cyanoethoxy-(N,N-diisopropylamino)-phosphane is added dropwise within ca. 3 minutes under $N_2$. The reaction mixture is stirred for 30 minutes at room temperature, then ca. 10 ml aqueous 5% $NaHCO_3$ solution is added and afterwards it is extracted twice with ca. 10 ml dichloromethane each time. The combined organic phases are dried over $Na_2SO_4$, the solvent is removed by distillation and the residue is chromatographed on silica gel 60 H using the mobile solvent $CH_2Cl_2$/ethyl acetate/triethylamine, 45:45:10.

Yield: 380 mg=94% of theoretical yield.

TLC (silica gel, mobile solvent dichloromethane/ethyl acetate/triethylamine 45:45:10): $R_f$=0.42 and 0.45 (2 diastereomers).

$^{31}$P-NMR ($d_6$DMSO): 147 and 152 ppm (2 diastereomers).

EXAMPLE 14

Solid Phase Synthesis of the Oligonucleotide d($AAA^{9i}G$) via Phosphoramidite

The synthesis of the oligonucleotide was carried out on a 1 µmol scale using the commercially available 5'-O-(4,4'-dimethoxy-trityl)-$N^6$-benzoyl-2'-deoxy-adenosine-3'-[(2-cyanoethoxy)-N,N-di-isopropylamino]phosphine and the phosphoramidite obtained in example 12 according to the standard protocol for the DNA-synthesizer 380 B from the Applied Biosystems Company (User Manual). The cleavage of the 5'-tritylated oligomer from the carrier material is carried out at room temperature in 25% aqueous ammonia solution.

The protecting groups of the exocyclic amino groups on the heterocycle were removed by a 16 hour treatment with 25% aqueous ammonia solution at 60° C. The 4,4'-dimethoxytrityl protecting group of the oligomer was cleaved by treatment with 80% acetic acid during 5 minutes at room temperature.

The oligonucleotide was purified by means of HPLC on a RP-18 column using the following mobile solvent system:

Mobile solvent A: 5% acetonitrile in 0.1 M triethylammonium acetate buffer, pH 7.0 Mobile solvent B: 100% acetonitrile Gradient 25 minutes 0–20% B in A It was desalted on a RP-18 silica gel column by firstly removing inorganic material by washing with water and then the oligomer was eluted with a mixture of methanol/water (3:2).

Yield: 5.5 $A_{260}$ units=ca. 50% of theoretical yield.

EXAMPLE 15

Chemical Solid Phase Synthesis of the Oligonucleotide d($AAAA^{Cl}A$) via Phosphonate The synthesis of this oligonucleotide with a 2-chloroadenosine building block ($^{Cl}A$) was carried out on a synthesis scale of 1 µmol using the commercially available 5'-O-(4,4-dimethoxytrityl)-$N^6$-benzoyl-2'-deoxy-adenosine-3'-phosphonate and the phosphonate from example 10 according to a standard protocol (User Bulletin 47, 1988) on a DNA synthesizer 380 B from the Applied Biosystems Company.

The oligomer was processed and purified as described in example 13.

Yield: 3 $A_{260}$ units=ca. 25% of theoretical yield.

EXAMPLE 16

Photochemical Conversion of the Oligonucleotide from Example 15

2.0 $A_{260}$ units of the oligomer from example 14 were dissolved in 0.1 ml redistilled water and irradiated with a 4 W mercury resonance lamp (Heraeus) with a light intensity of $1.79 \times 10^{17}$ quanta×$min^{-1}$×$cm^{-2}$. An almost quantitative conversion into the oligomer containing 2'-deoxy-isoguanosine was achieved after 45 minutes according to the HPLC result.

The product proved to be identical when co-injected with the oligomer of example 14.

EXAMPLE 17

2-Bromo-9-(2-deoxy-β-D-erythro-pentofuranosyl)-6-{[(dimethylamino)methylidene]amino}-9H-purine The compound was produced analogously to example 8 except that the following amounts were used: 2-bromo-2'-deoxyadenosine (330 mg, 1.0 mmol), DMF (3 ml), dimethylformamide-diethylacetal (0.85 ml, 5 mmol). Colourless amorphous solid (306 mg, 80%). TLC ($CH_2Cl_2$/MeOH, 9:1): $R_f$ 0.33. UV (MeOH): 318 (28600), 238 (13000). $^1$H-NMR (($D_6$(DMSO): 2.32, 2.67 (2m, H—C(2')); 3.14, 3.23 (2s, $CH_3$—N); 3.56 (m, H—C(5')); 3.86 (m, H—C(4')); 4.39 (m, H—C(3')); 4.95 (t, J=5.5 Hz, HO—C(5')); 5.33 (d, J=4.3 Hz, HO—C(3')); 6.31 ("t", J=6.3 Hz, H—C(1')); 8.44 (s, H—C(8)); 8.85 (s, H—C(N=)). Anal. calc. for $C_{13}H_{17}BrN_6O_3$ (385.22): C, 40.53; H, 4.45; N, 21.82; found: C, 40.66; H, 4.50; N, 21.79.

EXAMPLE 18

2-Bromo-9-[2-deoxy-5-O-(4,4'-dimethoxytrityl)-β-D-erythro-pentofuranosyl]-6-{[(dimethylamino)methylidene]amino}-9H-purine The compound was produced as described in example 9. The following were used: compound from example 17 (250 mg, 0.65 mmol), pyridine (2 ml), 4,4'-dimethoxytrityl chloride (330 mg, 0.98 mmol). FC cf. 9. Colourless solid (260 mg, 58%). TLC ($CH_2Cl_2$/MeOH, 9:1): $R_f$ 0.37. $^1$H-NMR (($D_6$)DMSO): 2.23, 2.68 (2m, H—C(2')); 3.01, 3.09 (2s, $CH_3$—N); 3.57, 3.58 (2s, $CH_3$O); 3.84 (m, H—C(4')); 4.33 (m, H—C(3')); 5.24 (d, J=4.5 Hz, HO—C(3')); 6.22 ("t", J=5.8 Hz, H—C(1')); 6.6–7.2 (m, aromat. H); 8.21 (s, H—C(8)); 8.69 (s, H—C(N=)). Anal. calc. for $C_{34}H_{35}BrN_6O_5$ (687.59): C, 59.39; H, 5.13; N, 12.22; found: C, 59.46; H, 5.40; N, 12.09.

EXAMPLE 19

9-[2-Deoxy-3-(triethylammonium phosphonate)-5-O-(4,4'-dimethoxytrityl)-β-D-erythro-pentofuranosyl]-6-[(dimethylamino)methylidene]-9H-isoguanine 1,2,4-Triazole (716 mg, 10 mmol) is added to a solution of $PCl_3$ (270 μl, 3.1 mmol) and N-methylmorpholine (3.5 ml) in $CH_2Cl_2$ (25 ml). After stirring for 30 minutes it is cooled to 0° C. and the compound of example 11 (413 mg, 0.64 mmol) dissolved in $CH_2Cl_2$ (25 ml) is slowly added. After stirring for 30 minutes at room temperature, the mixture is added to 1 mol/l $(Et_3NH)HCO_3$ (35 ml), shaken and the phases are separated. The aqueous phase is extracted with $CH_2Cl_2$ (3×30 ml). The combined organic extracts are dried and the colourless foam is separated on four preparative silica gel plates (20×20 cm) and developed in $CH_2Cl_2$—MeOH-triethylamine 80:10:5. The residue from the main zone yields a colourless foam (320 mg, 63%). TLC ($CH_2Cl_2$/MeOH/$Et_3N$, 80:10:5): $R_f$ 0.40. $^1$H-NMR ($D_6$)DMSO): $^1$H-NMR (($D_6$)DMSO): 1.1–1.2 (m, $CH_3CH_2$—N); 2.25, 2.65 (2m, H—C(2')); 2.7–2.8 (m, $CH_3CH_2$N); 3.16, 3.25 (2s, $CH_3$—N); 3.25 (s, H—C(5')); 3.77, 3.78 (2s, $CH_3$O); 4.16 (m, H—C(4')); 4.79 (m, H—C(3')); 6.20 ("t", J=6 Hz, HO—C(5')); 6.8–7.4 (m, aromat. H); 7.97 (s, H—C(8)); 9.15 (s, H—C(N=)). $^{31}$P-NMR (($D_6$)DMSO): 2.23 ($^1$J(PH)=585 Hz, $^3$J(PH)=8.1 Hz). Anal. calc. for $C_{40}H_{52}N_7O_8P$ (789.87): C, 60.82, H, 6.63; N, 12.41; found: C, 60.80; H, 6.79; N, 12.41.

EXAMPLE 20

2-Bromo-9-[2-deoxy-3-(triethylammonium-phosphonate)-5-O-(4,4'-dimethoxytrityl)-β-D-erythro-pentofuranosyl]-6-{[(dimethylamino)methylidene]amino}-9H-purine The phosphonate is produced analogously to example 19 from the compound according to example 18. Colourless foam (128 mg, 48%). TLC ($CH_2Cl_2$/MeOH/N($Et)_3$, 88:10:2): $R_f$ 0.35. $^1$H-NMR (($D_6$)DMSO): 1.0–1.2 (m, $CH_3CH_2$—N); 2.23, 2.82 (2m, H—C(2')); 2.7–2.9 (m, $CH_3CH_2$N), 3.14, 3.23 (2s, $CH_3$—(N=)); 3.70, 3.71 (2s, $CH_3$O); 4.14 (m, H—C(4')); 4.72 (m, H—C(3')); 6.31 ("t", J=6.2 Hz, H—C(1')); 6.63 (d, H—P, J=585 Hz); 6.7–7.3 (m, aromat. H); 8.31 (s, H—C(8)); 8.82 (s, H—C(N=)). $^{31}$P-NMR (($D_6$) DMSO): 0.90 ($^1$J(PH)=585 Hz, $^3$J(PH)=9.1 Hz).

EXAMPLE 21

2-Chloro-9-(2-deoxy-β-D-erythro-pentofuranosyl)-6-methylamino-9H-purine

A suspension of 3',5'-bis-toluoyl-2,6-dichloropurine-riboside (A) (1.08 g, 2 mmol) in $CH_3N$/MeOH (1:5, 30 ml) is stirred for two days at room temperature. The reaction mixture is evaporated to dryness in a vacuum and the residue is chromatographed on a silica gel column (2×25 cm, $CH_2Cl_2$—MeOH (9:1)). Colourless needles are obtained from water (430 mg, 72%). M.p. 163–165° C. TLC ($CH_2Cl_2$—MeOH, 9:1): $R_f$ 0.35. UV (water): 270 (16800). $^1$H-NMR (($D_6$)DMSO): 2.30, 2.65 (2m, $H_2$—C(2')); 2.92 (d, J=4.1 Hz, $CH_3$—N), 3.55 (m, $H_2$—C(5')); 3.86 (m, H—(C-4')); 4.39 (m, H—(C-3')); 4.96 (t, J=5.3 Hz, OH—C(5')); 5.32 (d, J=4.0 Hz, OH—C(3')); 6.27 ("t", J=6.8 Hz, H—C(1')); 8.26 (d, J=4.2 Hz, NH); 8.35 (s, H—C(8). Anal. calc. for $C_{11}H_{14}ClN_5O_3$ (299.7): C, 44.08; H, 4.71; N, 23.27; found: C, 43.96; H, 4.90; N, 23.24.

EXAMPLE 22

2-Chloro-9-(2-deoxy-β-D-erythro-pentofuranosyl)-6-hydroxyethylamino-9H-purine

Hydroxyethylamine (915 mg, 15 mmol) is reacted with (A) (810 mg, 1.5 mmol) in MeOH (25 ml) as described in example 21. Colourless needles (310 mg, 63%) from EtOAc/acetone. M.p. 167–168° C. TLC ($CH_2Cl_2$—MeOH, 9:1): $R_f$ 0.15. UV (water): 271 (18700). $^1$H-NMR (($D_6$) DMSO): 2.30 and 2.65 (2m, H—C(2')); 3.56 (m, H—C(5'), H—$CH_2$(N)); 3.86 (q, H—C(4')); 4.39 (bs, H—C(3')); 4.76 (t, J=4.6 Hz, OH—C(ethyl)); 4.95 (t, J=5.5 Hz, OH—C(5')); 5.30 (d, J=4.1 Hz, OH—C(3')); 6.27 (t, J=6.7 Hz, H—C(1')); 8.13 (bs, H—N(6)); 8.35 (s, H—C(8). Anal. calc. for $C_{12}H_{16}ClN_5O_4$ (329.7): C, 43.71; H, 4.89; N, 21.24; found: C, 43.59; H, 4.80; N, 21.09.

EXAMPLE 23

2-Chloro-6-butylamino-9-(2-deoxy-β-D-erythro-pentofuranosyl)-9H-purine

Compound (A) (540 mg, 1 mmol) in MeOH (15 ml) is reacted at 37° C. with N-butylamine (730 mg, 10 mmol) as described in example 21. It is purified on 20×20 cm preparative silica gel plates using $CH_2Cl_2$—MeOH (9:1) as the mobile solvent. A colourless solid is obtained (210 mg, 61%) which crystallizes as needles (water). M.p. 159° C. TLC ($CH_2Cl_2$—MeOH, 9:1): $R_f$ 0.50. UV (water): 271 (18800). $^1$H-NMR (($D_6$)DMSO): 0.88, 1.31, 1.56, 3.40 (m, aliphat. H); 2.27 and 2.63 (2m, H—C(2')); 3.56 (m, H—C(5')); 3.86 (bs, H—C(4')); 4.40 (bs, H—C(3')); 4.95 (t, J=5.3 Hz, OH—C(5')); 5.30 (d, J=3.8 Hz, OH—C(3')); 6.27 ("t", J=6.7 Hz, H—C(1')); 8.30 (bs, H—N(6)); 8.34 (s, H—C(8). Anal. calc. for $C_{14}H_{20}ClN_5O_3$ (341.8): C, 49.20; H, 5.90; N, 24.49; found: C, 49.16; H, 5.85; N, 24.30.

EXAMPLE 24

2-Chloro-6-cyclohexylamino-9-(2-deoxy-β-D-erythro-pentofuranosyl)-9H-purine

Cyclohexylamine (1.0 g, 10 mmol) is added to a stirred solution of compound (A) (1.08 g, 2 mmol) in MeOH (30 ml). It is stirred for a further two days at room temperature. The reaction mixture is reacted with sodium methoxide (3 ml, 1 mol/l in MeOH) and stirred for a further day. The reaction mixture is evaporated in a vacuum (oil) and purified chromatographically on a silica gel column (2.5×25 cm, using $CH_3Cl$—MeOH (9:1) as the mobile solvent). The fractions containing nucleoside are evaporated to dryness in a vacuum. The residue yields colourless crystals from EtOAc. (460 mg, 63%). M.p. 160–162° C. TLC ($CH_2Cl_2$—MeOH), 9:1): $R_f$ 0.63. UV (water): 273 (19600). $^1$H-NMR (($D_6$)DMSO): 1.0–2.0 (m, H-(cyclohexyl)); 2.25 and 2.60 (2m, H—C(2')); 3.55 (m, H—C(5')); 3.86 (q, H—C(4')); 4.38 (bs, H—C(3')); 4.97 (t, J=5.6 Hz, OH—C(3')); 5.32 (d, J=4.2 Hz, OH—C(5')); 6.26 ("t", J=6.6 Hz, H—C(1')); 8.15 (d, J=8.4 Hz, H—N(6)); 8.34 (s, H—C(8). Anal. calc. for $C_{16}H_{22}ClN_5O_3$ (367.8): C, 52.24; H, 6.03; N, 19.04; found: C, 52.11; H, 5.96; N, 18.88.

EXAMPLE 25

2-Chloro-6-benzylamino-(2-deoxy-β-D-erythro-pentofuranosyl)-9H-purine

Benzylamine (1.07 g, 10 mmol) is reacted with compound (A) (920 mg, 1.7 mmol) in MeOH (30 ml) as described in example 24. It is purified by chromatography on a silica gel column (3×24 cm, EtOAc (200 ml) and EtOAc-MeOH (9:1) as the mobile solvent). Colourless crystals are obtained from EtOH/water (390 mg, 61%). M.p. 147° C. TLC ($CH_2Cl_2$—MeOH, 9:1): $R_f$=0.60. UV (water): 273 (21600). $^1$H-NMR (($D_6$)DMSO): 2.30 and 2.60 (2m, H—C(2')); 3.53 (m, H—C(5')); 3.85 (q, H—C(4')); 4.39 (bs, H—C(3')); 4.64 (d, J=5.7 Hz, H—($CH_2$)); 4.96 (t, J=5.9 Hz, OH—C($5^1$)); 5.33 (d, J=4.2 Hz, OH—C(3')); 6.27 ("t", J=6.6 Hz, H—C(1')); 7.25–7.32 H—C(phenyl)); 8.37 (s, H—C(8)); 8.89 (t, J=4.8 Hz, H—N(6)); Anal. calc. for $C_{17}H_{18}ClN_5O_3$ (375.8): C, 54.33; H, 4.83; N, 18.64; found: C, 54.27; H, 4.85; N, 18.54.

EXAMPLE 26

2-Chloro-9-[2-deoxy-β-D-erythro-pentofuranosyl]-6-methoxy-9H-purine

A suspension of compound (A) (810 mg, 1.5 mmol) in MeOH (30 ml) is treated with sodium methoxide/MeOH (4.5 ml, 1 mol/l) and stirred for 3 hours at room temperature. After 30 minutes a clear solution forms. The reaction mixture is evaporated and the residue is eluted on a silica gel column 60 H (3×22 cm using EtOAc (200 ml) and EtOAc-MeOH (9:1) as the mobile solvent). The fractions containing nucleoside are pooled, evaporated in a vacuum and the residue is crystallized from EtOAc. Colourless crystals are obtained (290 mg, 64%). M.p. 141–142° C. TLC ($CH_2Cl_2$—MeOH, 9:1): $R_f$=0.54. UV (water): 258 (12300). $^1$H-NMR (($D_6$)DMSO): 2.35 and 2.70 (2m, H—C(2')); 3.56 (m, H—C(5')); 3.85 (q, H—C(4')); 4.10 (s, H—C(6-$OCH_3$)); 4.42 (bs, H—C(3')); 4.94 (t, J=5.5 Hz, OH—C(5')); 5.36 (d, J=4.3 Hz, OH—C(3')); 6.35 ("t", J=6.6 Hz, H—C(1')); 8.60 (s, H—C(8)). Anal. calc. for $C_{11}H_{13}ClN_4O$ (300.7): C, 43.94; H, 4.36; N, 18.63; found: C, 44.08; H, 4.45; N, 18.63.

EXAMPLE 27

6-Amino-2-chloro-9-[2-deoxy-3,5-(di-O-acetyl)-β-D-erythro-pentofuranosyl]-9H-purine A stirred suspension of 2-chloro-2'-deoxyadenosine (850 mg, 3 mmol) in pyridine (10 ml) is treated with acetic anhydride (10 ml) during which the starting material dissolves within 30 minutes. After 3 hours, the mixture is evaporated in a vacuum (oil), taken up three times in toluene/EtOH and evaporated. The oily residue is dried in a high vacuum and crystallized from EtOH. (1.03 g, 92%). M.p. 173–175° C. TLC ($CH_2Cl_2$—MeOH, 95:5): $R_f$=0.52. UV (MeOH/$H_2O$): 264 (15300). $^1$H-NMR (($D_6$)DMSO): 1.82 and 2.01 (2s, H—($CH_2CO$)); 2.55 and 3.00 (2m, H—C(2')); 4.25 (m, H—C(4') and H—C(5')); 5.37 (m, H—C(3')); 6.29 ("t", J=6.5 Hz, H—C(1')); 7.85 (s, $NH_2$); 8.37 (s, H—C(8)). Anal. calc. for $C_{14}H_{16}ClN_5O_5$ (369.8): C, 45.48; H, 4.06; N, 18.94; found: C, 45.61; H, 4.12; N, 18.90.

EXAMPLE 28

6-Amino-8-bromo-2-chloro-9-[2-deoxy-3,5-(di-O-acetyl)-β-D-erythro-pentofuranosyl]-9-H-purine A solution of 3,5-diacetyl-2-chloro-2-deoxyadenosine (400 mg, 1.08 mmol) in dioxane (16 ml) and aqueous sodium acetate (pH 4.7, 0.5 M, 4 ml) is stirred and a solution of $Br_2$ (240 mg, 1.5 mmol) in dioxane is added within 15 minutes. It is stirred for a further 15 minutes (monitored by TLC). The mixture is diluted with $CHCl_3$ (50 ml) and with water (50 ml), sodium bicarbonate (50 ml, sat.), 1% $Na_2S_2O_4$ (50 ml) and water (2×50 ml). The organic phase is dried over $Na_2SO_4$ and evaporated to dryness. The residue is crystallized from EtOH. Colourless crystals of (8) are formed. (370 mg, 76%). M.p. 163–164° C. TLC ($CH_2Cl_2$—MeOH, 95:5): $R_f$=0.65. UV (MeOH/$H_2O$, 1:1): 269 (17500). $^1$H-NMR (($D_6$)DMSO): 1.95 and 2.09 (2s, H—C($CH_2CO$); 2.55 and 3.45 (2m, H—C(2')); 4.17 (m, H—C(5')); 4.34 (m, H—C(4')); 5.33 (q, H—C(3')); 6.29 ("t", J=6.8 Hz, H—C(1')); 7.96 (s, $NH_2$). Anal. calc. for $C_{14}H_{15}BrClN_5O_5$ (448.7): C, 37.48; H, 3.37; N, 15.61; found: C, 37.63; H, 3.43; N, 15.66.

EXAMPLE 29

6-Amino-8-bromo-2-chloro-9-(2-deoxy-β-D-erythro-pentofuranosyl)-9H-purine(8-bromo-2-chloro-2'-deoxyadenosine)

Ammonia in methanol (10 ml, saturated at 0° C.) is added to a solution of the compound from example 28 (300 mg, 0.67 mmol) in MeOH (10 ml). The reaction mixture is stirred at 4° C. overnight. Light-yellow chromatographically-pure crystals are formed (192 mg, 79%). An analytical sample is crystallized from ethanol. 190° C. (decomp.). TLC ($CH_2Cl_2$—MeOH, 9:1): $R_f$=0.57. UV (water): 269 (16300). $^1$H-NMR (($D_6$)DMSO): 2.20 and 3.15 (2m, H—C(2')); 3.45 and 3.62 (2m, H—C(5')); 3.82 (q, H—C(4')); 4.45 (bs, H—C(3')); 4.85 (t, J=6.2 Hz, OH—C(5')); 5.35 (d, J=4.2 Hz, OH—C(3')); 6.23 ("t", J=7.1 Hz, H—C(1')); 7.99 (s, $NH_2$). Anal. calc. for $C_{10}H_{11}BrClN_5O_3$ (364.6): C, 32.94; H, 3.04; N, 19.21; found: C, 33.12; H, 3.11; N, 19.22.

EXAMPLE 30

6-[(Dimethylamino)methylidene]-9-(β-D-ribofuranosyl)-9H-isoguanine 1000 mg (3.53 mmol) isoguanosine is dissolved in 50 ml absolute DMF, 10 ml (58.7 mmol) N,N-dimethylformamide-diethylacetal is added and it is stirred for 12 hours at room temperature. Subsequently the solvent is removed in a vacuum and the residue is evaporated several times firstly with toluene then with acetone. The residue is purified by column chromatography (silica gel, column: 25×4.5 cm, mobile solvent $CH_2Cl_2$/MeOH 6:4). The residue of the main zone is crystallized from methanol. 1054 mg (88.3%) colourless, amorphous crystals which melt above 230° C. while decomposing. TLC ($CH_2Cl_2$/MeOH 3:2): $R_f$ 0.45. UV (MeOH: max 340, 238 nm. 4.8 (m, H—C(3')); 4.53 (m, H—C(2')); 5.11 (d, HO—C(3')); 5.41 (d, HO—C(2')); 5.59 (t, HO—C(5')); 5.65 (d, H—C(1')); 8.05 (s, H—C(8)); 9.16 (s, H—C(N=)); 11.12 (br, s, H—N).

$C_{13}H_{18}N_6O_5$ (338.33): calc. C, 46.15; H, 5.36; N, 24.84; found C, 46.42; H, 5.47; N, 24.75.

EXAMPLE 31

6-[(Dimethylamino)methylidene]-9-[5-O-(methoxytriphenyl-methyl)-β-D-ribofuranosyl]-9H-isoguanine 150 mg (0.44 mmol) of the compound from example 30 is dried by evaporating twice with absolute pyridine and it is dissolved in 25 ml absolute pyridine while heating. 206 mg (0.67 mmol) monomethoxytrityl chloride and 227 mg (1.76 mmol) N-ethyldiisopropylamine are added to the hot solution. The reaction mixture is stirred for 12 hours at 60° C. and subsequently 5 ml methanol is added. It is shaken out with 20 ml 5 percent $NaHCO_3$ solution and extracted 5 times with 10 ml $CH_2Cl_2$ in each case. The combined extracts are concentrated and chromatographed on silica gel (column: 15×1.5 cm, mobile solvent: $CH_2Cl_2$/MeOH 83:17). 136.4 mg (50.4%) colourless amorphous substance. TLC ($CH_2Cl_2$/MeOH, 83:17): $R_f$ 0.50. $^1$H-NMR ($D_6$-DMSO): 3.08, 3.16 (2s, $CH_3$—N); 3.72 (s, $CH_3$O); 4.00 (m, H—C(4')); 4.16 (m, H—C(3')); 4.49 (m, H—C(2')); 5.16 (d, HO—C(3')); 5.56 (d, HO—C(2')); 5.73 (d, H—C(1')); 6.64 (d, H—C(5')); 7.20–7.37 (m, 14 arom. H); 7.96 (s, H—C(8); 9.13 (s, H—C(N=)); 11.11 (br, s, NH).

$CH_{33}H_{34}N_6O_6$: calc. C, 64.90; H, 5.61; N, 13.76; found.

EXAMPLE 32

2-Amino-(2-deoxy-β-D-erythro-pentofuranosyl) adenine 5.0 g (18.6 mmol) deoxyguanosine is silylated for 10 hours at 145° C. with 200 ml hexamethyldisilazane (HMDS) and 0.5 ml trimethylchlorosilane (TCS) in the same manner as the corresponding ribo compound [2][3]. Subsequently excess HMDS is removed by distillation under normal pressure. The remaining turbid syrup ([2]) is taken up in a mixture of 30 ml absolute toluene and 2 ml HMDS. This mixture is transferred into a 300 ml autoclave. After addition of 4 ml of a 0.5 M solution (2 mmol) of tris(trimethyl) silyltriflate in absolute toluene, it is pressurized for 0.5 hours with $NH_3$ (5 bar) at 0° C.; then it is heated for 48 hours at 145° C. (external temperature regulation). After cooling to room temperature, the $NH_3$ is carefully vented. The solid residue is suspended in 150 ml methanol (ultrasonic bath), admixed with 150 ml water and transsilylated for 4 hours at 100° C. After removing the methanol by distillation, 250 ml water is added, the solution is admixed with active charcoal, hot-filtered and rewashed with 100 ml hot water. The yellow filtrate is applied to a Dowex 1×2 column (20×2 cm, $OH^-$). Elution with 500 ml water yields a main zone from which the product (1.2 g, 24.2%) is obtained after evaporation as a yellow powder. The product is identical with an authentic sample [1][4–6]. TLC (silica gel, $CH_2Cl_2$/MeOH 4:1): $R_f$=0.4. UV (MeOH):=$\lambda_{max}$ 217 (23500), 256 (8900), 282 (9900). $^{13}$C-NMR in (($D_6$)DMSO): 160.2 C(6); 156.3 C(2); 151.3 C(4); 135.9 C(8); 113.5 C(5); 87.8 C(4'); 83.2 C(1'); 71.1 C(3'); 62.1 C(5').

EXAMPLE 33

6-Amino-9-(2-deoxy-β-D-erythro-pentofuranosyl)-1, 9-dihydro-2H-purin-2-one(2'-deoxyisoguanosine)

A solution of 300 mg (4.3 mmol) sodium nitrite in 5 ml hot $H_2O$ is admixed with 300 mg (1.1 mmol) of the compound from example 32 analogously to the ribonucleoside [7] and a total of 0.45 ml (7.8 mmol) glacial acetic acid is slowly added dropwise (foaming!). After 5 minutes it is diluted with 10 ml $H_2O$ and adjusted to pH 8 with dilute ammonia and then a further 300 ml $H_2O$ is added. It is adsorbed to a Serdolit AD-4 ion exchanger (Serva Germany, 4×22 cm) and washed with 500 ml $H_2O$. A mixture of about 500 ml $H_2O$/i-PrOH (95:5) elutes the main zone from which the compound is obtained as a slightly yellow powder (120 mg, 40.8%) after evaporation. TLC (silica gel, $H_2O$-saturated n-butanol): $R_f$ 0.25. UV (MeOH): $\lambda_{max}$ 248 (8100), 297 (9900). $^{13}$C-NMR in (($D_6$)DMSO): 156.4 C(6); 137.7 C(8); 153.0 C(2); 109.8 C(5); 88.1 C(4'); 83.9 C(1'); 71.2 C(3'); 62.0 C(5')[8].

EXAMPLE 34

Silylation of 6-[(dimethylamino)methylidene]-9-[5-O-(4-methoxytriphenyl-methyl)-β-D-ribofuranosyl]-9H-isoguanine with Triisopropylsilyl Chloride 150 mg (0.24 mmol) 5'-monomethoxytriethyl-N-6-dimethylaminomethylidene-isoguanosine is dried by evaporating twice with pyridine, it is dissolved in 2 ml absolute pyridine and 62 mg (0.36 mmol) silver nitrite is added. After the silver nitrite has dissolved 0.05 ml (0.25 mmol) triisopropylsilyl chloride in 5 ml tetrahydrofuran is added under an argon atmosphere. The reaction mixture is stirred for 12 hours at room temperature under an inert gas atmosphere in the dark. Afterwards 0.025 ml (0.125 mmol) triisopropyl chloride and 20 mg (0.12 mmol) silver nitrite is again added. After 30 hours it is neutralized with 10 ml $NaHCO_3$ solution (5%) and extracted four times with 10 ml dichloromethane in each case. The combined extracts are dried over sodium sulfate and concentrated. The residue is separated chromatographically. 2=2'-triisopropylsilyl-5'-monomethoxytrityl-N-6-dimethylaminomethylidene-isoguanosine is obtained from the main zone with an $R_f$=0.55 (silica gel, EtOAc/$CH_2Cl_2$, 4:1). The regioisomer is formed in a small amount.

2'-silylisomer: $^1$H-NMR ($D_6$-DMSO): 11.05 (br, s, NH); 9.11 (s, N=CH); 7.99 (s, H—C(8)); 7.66–6.84 (m, arom. CH); 5.79 (d, H—C(1')); 5.06 (d, HO—C(3')); 4.77 (m, H—C(2')); 4.21 (m, H—C(3')); 4.03 (m, H—C(4')); 3.72 (s, $OCH_3$); ca. 3.25 (m, H—C(5')); 3.19 and 3.09 (2s, 2 N—$CH_3$); 0.96 and 0.91 (m, Si—C($CH_3$)$_3$); 3.25 (m, 5'-$CH_2$); 3.19, 3.09 (2s, [N—($CH_3$)$_2$]); 0.9 (m, Si[CH—($CH_3$)$_2$]).

EXAMPLE 35

6-Amino-2-chloro-7-(2-deoxy-β-D-erythro-pentofuranosyl)-purine

A solution of 2,6-dichloro-7-(2'-deoxy-3',5'-di(O-(p-toluoyl)-β-D-erythro-pentofuranosyl)-purine (600 mg, 1.11 mmol) in methanolic ammonia (60 ml, saturated at 0° C.) is stirred for 24 hours at 80° C. The mixture is evaporated in a vacuum and the residue is chromatographed on silica gel 60 H (column: 15×4 cm). Crystallization from MeOH/iso-PrOH affords colourless crystals (210 mg, 66.5%) with a melting point of >250° C. UV (MeOH): $\lambda_{max}$ 276 nm (ε=7200). $^1$H-NMR (($D_6$)DMSO) δ=2.30 and 2.40 (m, 2'-H). 3.56 (m, 5'-H); 3.92 (m, 4'-H); 4.40 (m, 3'-H); 5.18 (t, J=5.0 Hz, 5'-OH); 5.42 (d, J=4.5 Hz, 3'-OH); 6.31 (pt, J=6.5 Hz, 1'-H); 7.48 (s, $NH_2$); 8.56 (s, 8-H). $C_{10}H_{12}N_5O_3Cl$ (285.67) calc. C, 42.05; H, 4.23; N, 24.51; found C, 42.08; H, 4.25; N, 24.58.

EXAMPLE 36

7-(2-Deoxy-β-D-erythro-pentofuranosyl)-7H-isoguanine 1 ml aqueous ammonia solution is added to a solution of the compound from example 35 (44 mg, 0.16 mmol) in water (75 ml). The mixture is irradiated for eight hours in a quartz container with UV light. The solution is evaporated in a vacuum and the residue is dissolved in water (50 ml) and chromatographed on a XAD-4 column (3×20 cm). The column is washed with water (500 ml) and the product is eluted with water/isopropanol (1:1). The fractions containing nucleotide are pooled, evaporated in a vacuum and crystallized from ethanol.

[1] Sigma Chemie GmbH, 8024 Deisenhofen, Germany.

[2] H. Vorbrüggen, K. Krolikiewicz, Liebigs Ann. Chem. 1976, 745

[3] M. J. Robins, F. Hansske, S. E. Bernier, Can. J. Chem. 1981, 59

[4] R. H. Iwamoto, E. M. Acton, L. Goodman, J. Med. Chem. 1963, 6, 684.

[5] J. A. Montgomery, K. Hewson, J. Med. Chem. 1969, 12, 498.

[6] R. Fathi, B. Goswami, Pei-Pei Kung, B. L. Gaffney, R. A. Jones, Tetrahedron Lett. 1990, 31, 319.

[7] J. Davoll, J. Am. Chem. Soc. 1951, 73, 3174.

[8] Z. Kazimierczuk, R. Mertens, W. Kawozynski, F. Seela, Helv. Chim. Acta 1991, 74, 1742.

What is claimed is:

1. An oligonucleotide capable of forming a parallel duplex structure, which comprises a structure selected from the group consisting of:

(i)

(ii)

(iii)

(iv) and (v)

wherein (1) $R_3$ is hydrogen or a protecting group, and

(2) W and Z are independently hydrogen, a halo group, a reporter group, an intercalator group, —NH(CH$_2$)$_n$NH$_2$ wherein n is a number from 2 to 12, or —R—CH$_2$COOH, wherein R is C$_1$–C$_8$ alkylenyl.

2. The oligonucleotide of claim 1, that consists of from 6 to 100 nucleotides.

3. The oligonucleotide of claim 1, wherein the reporter group is selected from the group consisting of biotin, digoxigenin and a fluorescent dye.

4. The oligonucleotide of claim 1, wherein the intercalator group is selected from the group consisting of phenanthroline, acridine, actinomycin, EDTA and psoralen.

5. A compound of formula wherein $R_1$ is hydrogen, a protecting group, PO$_3$H$_2$, P$_2$O$_6$H$_3$, P$_3$O$_9$H$_4$, or an alpha, beta, or gamma thiophosphate of PO$_3$H$_2$, P$_2$O$_6$H$_3$, or P$_3$O$_9$H$_4$, $R_2$ is hydroxy, phosphoramidite, methylphosphonate, H-phosphonate, a reporter group, or an intercalator group, with the proviso that $R_2$ is not hydroxy when $R_1$, $R_3$, W and Z are all hydrogen;

$R_3$ is hydrogen or a protecting group; and

W and Z are hydrogen, a halo group, —NH(CH$_2$)$_n$NH$_2$ or —NH(CH$_2$)$_n$NH-reporter group, wherein n is a number from 2 to 12, —R—CH$_2$COOH or —R—CH$_2$COO-reporter group, wherein R is C$_1$–C$_8$ alkylenyl, a reporter group, or an intercalator group.

6. A compound of formula wherein $R_1$ is hydrogen, a protecting group, $PO_3H_2$, $P_2O_6H_3$, $P_3O_9H_4$, or an alpha, beta, or gamma thiophosphate of $PO_3H_2$, $P_2O_6H_3$ or $P_3O_9H_4$, $R_2$ is hydrogen, $R_3$ is hydrogen or a protecting group, and W and Z are hydrogen, a halo group, —NH(CH$_2$)$_n$NH$_2$, wherein n is a number from 2 to 12, —R—CH$_2$COOH, wherein R is $C_1$–$C_8$ alkylenyl, a reporter group or an intercalator group, with the proviso that when is $R_1$ is $P_3O_9H_4$, Z is not hydrogen.

7. A compound of formula:

wherein $R_1$ is hydrogen, a protecting group, $PO_3H_2$, $P_2O_6H_3$, $P_3O_9H_4$, or an alpha, beta, or gamma thiotriphosphate of $PO_3H_2$, $P_2O_6H_3$ or $P_3O_9H_4$, $R_2$ is hydrogen, hydroxy, phosphoramidite, methylphosphonate, H-phosphonate, a reporter group or an intercalator group, $R_3$ is hydrogen or a protecting group, and Z is hydrogen, a halo group, —NH(CH$_2$)$_n$NH$_2$ or —NH(CH$_2$)$_n$NH-reporter group wherein n is a number from 2 to 12, —R—CH$_2$COOH or —R—CH$_2$COO-reporter group wherein R is $C_1$–$C_8$ alkylenyl, a reporter group or an intercalator group.

8. A compound of formula:

wherein $R_1$ is a protecting group, a triphosphate or an alpha, beta, or gamma thiotriphosphate, with the proviso that $R_1$ is not a triphosphate when $R_2$ is hydroxy, $R_3$ is hydrogen and Z is hydrogen;

$R_2$ is hydroxy, a methylphosphonate, a phosphoramidite, an H-phosphonate, a reporter group, or an intercalator group;

$R_3$ is hydrogen, or a protecting group, and

Z is hydrogen, a halo group, —NH(CH$_2$)$_n$NH$_2$ or —NH(CH$_2$)$_n$NH-reporter group wherein n is a number from 2 to 12, —R—CH$_2$COOH or —R—CH$_2$COO-reporter group wherein R is $C_1$–$C_8$ alkylenyl, a reporter group, or an intercalator group, with the proviso that if $R_2$ is a phosphoramidite or an H-phosphonate, then $R_1$ is not a protecting group.

9. A compound of formula wherein $R_1$ is $P_3O_9H_4$ or an alpha, beta, or gamma thiophosphate of $PO_3H_2$, $P_2O_6H_3$, or $P_3O_9H_4$, $R_2$ is hydrogen, $R_3$ is hydrogen or a protecting group, and Z is hydrogen, a halo group, NH(CH$_2$)$_n$NH$_2$ wherein n is a number from 2 to 12, or —R—CH$_2$COOH, wherein R is $C_1$–$C_8$ alkylenyl, a reporter group or an intercalator group, wherein Z is not hydrogen if $R_1$ is $P_3O_9H_4$ or H.

10. A process for making an oligonucleotide, comprising contacting a pre-existing oligonucleotide with a polymerase and the compound of any of claims 5–9, wherein $R_1$ in said compound is $P_3O_9H_4$ or an alpha, beta or gamma thiophosphate of $P_3O_9H_4$, to incorporate said compound into said pre-existing oligonucleotide.

11. The process of claim 10, wherein $R_2$ is hydrogen, hydroxy, a reporter group or an intercalator group.

12. The process of claim 10, wherein $R_2$ is hydrogen, hydroxy, a reporter group or an intercalator group, $R_3$ is hydrogen or a protecting group, Z is hydrogen, a halo group, —NH(CH$_2$)$_n$NH$_2$ wherein n is a number from 2 to 12, or —R—CH$_2$COOH, wherein R is $C_1$–$C_8$ alkylenyl, a reporter group or an intercalator group, with the proviso that at least one of $R_2$ or Z is hydrogen.

13. A method for joining a nucleotide to a first nucleotide, comprising contacting said first nucleotide with the compound of any of claims 5–9, wherein $R_1$ in said compound is a protecting group, and $R_2$ is a phosphoramidite, a methylphosphonate or an H-phosphonate, to incorporate said compound into a nascent nucleic acid molecule.

14. The process of claim 13, wherein $R_2$, is a methylphosphonate, a phosphoramidite, an H-phosphonate, a reporter group, or an intercalator group;

$R_3$ is hydrogen, or a protecting group, and

Z is hydrogen, a halo group, —NH(CH$_2$)$_n$NH$_2$ or —NH(CH$_2$)$_n$NH-reporter group wherein n is a number from 2 to 12, —R—CH$_2$COOH or —R—CH$_2$COO-reporter group wherein R is $C_1$–$C_8$ alkylenyl, a reporter group, or an intercalator group.

15. The method of claim 10, wherein said oligonucleotide is from 6 to 100 nucleotides in length.

* * * * *